United States Patent [19]

Jones

[11] Patent Number: 5,122,112
[45] Date of Patent: Jun. 16, 1992

[54] ANTIGEN-SPECIFIC REMOVAL OF CIRCULATING IMMUNE COMPLEXES

[75] Inventor: Frank R. Jones, Edmonds, Wash.

[73] Assignee: IMRE Corporation, Seattle, Wash.

[21] Appl. No.: 579,217

[22] Filed: Sep. 5, 1990

Related U.S. Application Data

[63] Continuation of Ser. No. 308,987, Feb. 8, 1989, abandoned, which is a continuation of Ser. No. 933,705, Nov. 21, 1986, abandoned.

[51] Int. Cl.$^5$ .......................................... A61M 37/00
[52] U.S. Cl. ..........:........................... 604/4; 604/5;
424/530; 210/691; 210/502.1; 436/501; 436/506; 436/828
[58] Field of Search ........................ 604/4–6; 210/660, 690, 691, 502.1; 424/101; 436/501, 828, 513, 506, 507; 435/973

[56] References Cited

U.S. PATENT DOCUMENTS

| | | | |
|---|---|---|---|
| 4,137,401 | 1/1979 | Lemieux et al. | 536/116 |
| 4,215,688 | 8/1980 | Terman et al. | 604/5 |
| 4,223,672 | 9/1980 | Terman et al. | 604/5 |
| 4,238,473 | 12/1980 | Lemieux et al. | 424/11 |
| 4,409,105 | 10/1983 | Hayashi et al. | |
| 4,464,165 | 8/1984 | Pollard, Jr. | 604/5 |
| 4,512,763 | 4/1985 | Schneider | 604/5 |
| 4,614,513 | 9/1986 | Bensinger | 604/6 |
| 4,617,262 | 10/1986 | Maxim et al. | 435/7 |
| 4,664,913 | 5/1987 | Mielke et al. | 424/101 |
| 4,681,870 | 7/1987 | Balint et al. | |
| 4,687,808 | 8/1987 | Jarrett et al. | 604/4 |
| 4,711,839 | 12/1987 | Singhal | 435/4 |
| 4,740,457 | 4/1988 | Parratt | 435/7 |
| 4,801,687 | 1/1989 | Ngo | 530/387 |
| 4,806,346 | 2/1989 | Hum et al. | 424/85.8 |
| 5,061,237 | 10/1991 | Gessler et al. | 604/5 |

FOREIGN PATENT DOCUMENTS

| | | |
|---|---|---|
| 0054799 | 6/1982 | European Pat. Off. |
| 079221 | 5/1983 | European Pat. Off. |
| 0088818 | 9/1983 | European Pat. Off. |
| 0100660 | 2/1984 | European Pat. Off. |
| 0131251 | 1/1985 | European Pat. Off. |
| 0165811 | 12/1985 | European Pat. Off. |
| 172018 | 2/1986 | European Pat. Off. |
| 0237659 | 9/1987 | European Pat. Off. |

OTHER PUBLICATIONS

Kimball, Introduction to Immunology, 1983, 22.
Kiprov et al. (1984) J. Biol. Res. Mod. 3:341–346.
Jones et al. (1984) J. Biol. Res. Mod. 3:286–292.
Besa et al. (1981) Am. J. Med. 71:1035–1040.

Primary Examiner—C. Fred Rosenbaum
Assistant Examiner—Mark O. Polutta
Attorney, Agent, or Firm—Townsend and Townsend

[57] ABSTRACT

Extracorporeal perfusion using an immunoadsorbent material specific for disease-related antigens is used for therapy of the disease state. Antibodies to particular antigens, including tumor antigens, viral antigens, and bacterial antigens, are used to prepare the immunoadsorbent material. Patients suffering from the disease are then treated by removing a flow of blood, separating the blood into plasma cellular components, passing the plasma through the immunoadsorbent material, recombining the treated plasma and cellular components of the blood, and returning the treated blood to the patient.

10 Claims, 2 Drawing Sheets

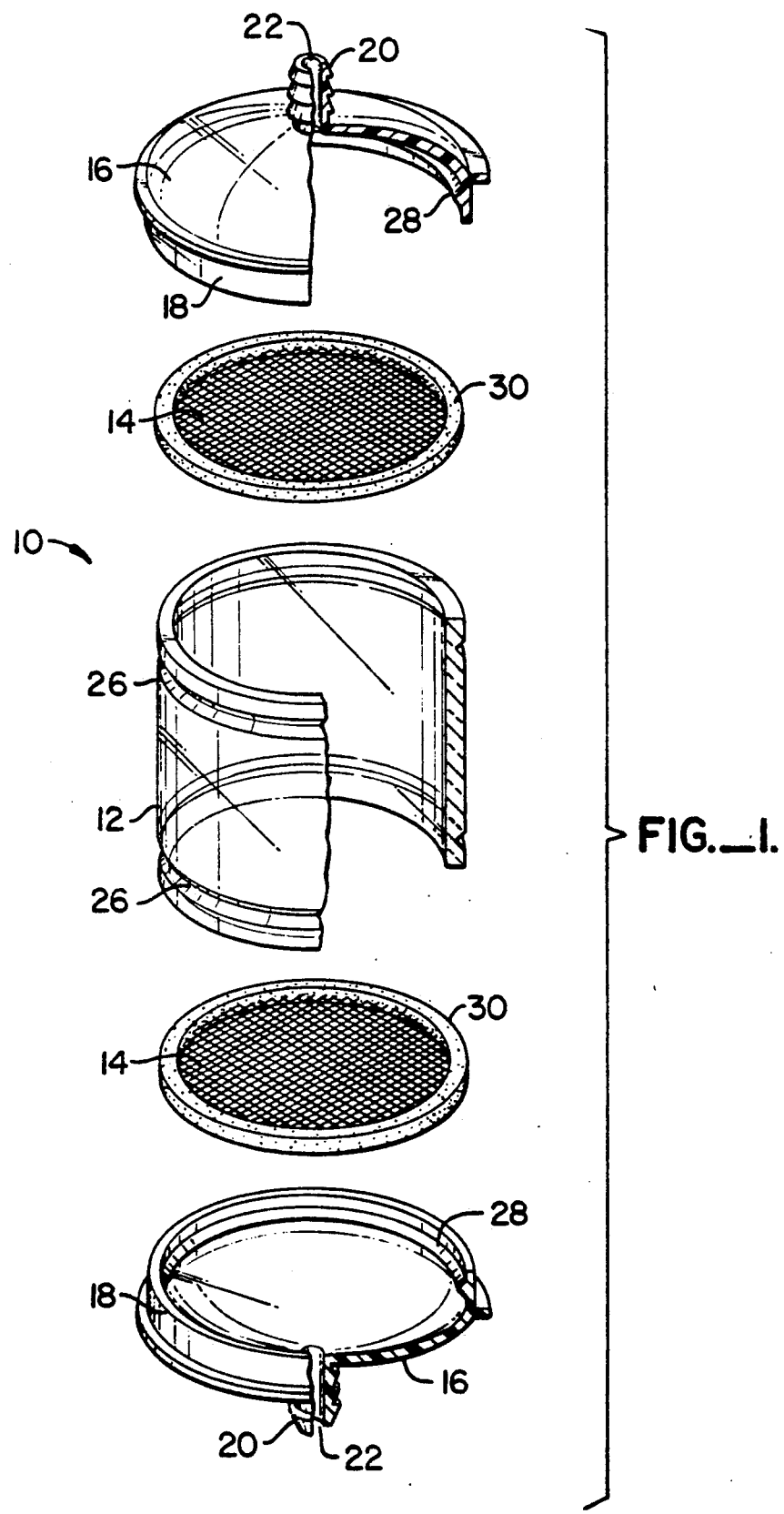

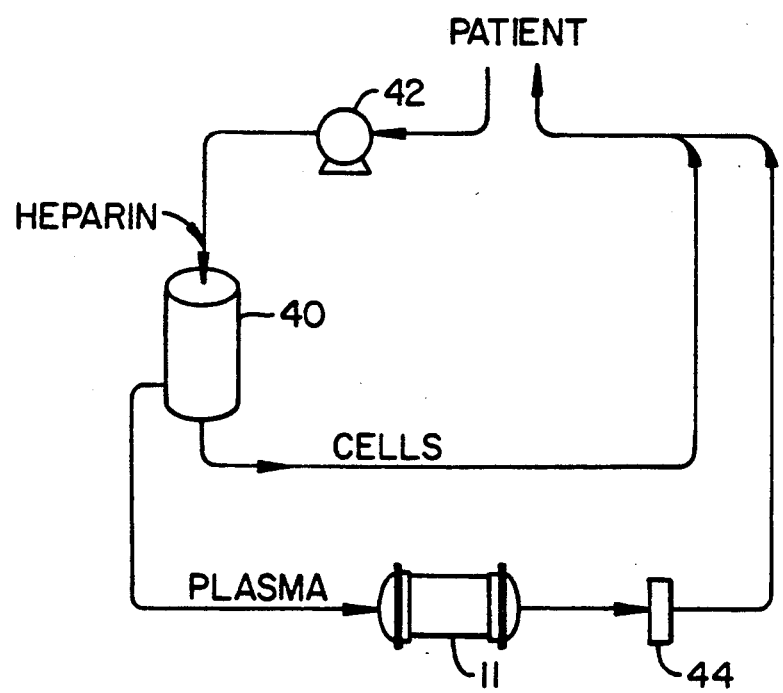
FIG._2.

ANTIGEN-SPECIFIC REMOVAL OF CIRCULATING IMMUNE COMPLEXES

This is a continuation of application Ser. No. 07/308,987, filed Feb. 8, 1989 which is a continuation of Ser. No. 06,933,705 filed Nov. 21, 1986, now abandoned.

BACKGROUND OF THE INVENTION

1. Field of the Invention

The present invention relates generally to the field of therapeutic plasma perfusion to remove substances from blood. More particularly, the invention relates to methods and materials for removing free antigen and circulating immune complexes including such antigen from blood for therapeutic purposes.

Plasma perfusion has been performed to remove a variety of toxic and harmful substances from blood in a non-specific manner. The process involves removing blood from a patient, separating the cellular components from the plasma constituent, and passing the plasma through an immunoadsorbent column to remove the desired substances. The cellular blood components and treated plasma are then returned to the patient, either together or separately. Alternatively, the cellular components may be combined with other replacement plasma and reinfused into the patient. Particular applications have been the removal of poisons, overdosed drugs, cholesterol, immune complexes, autoimmune antibodies, rheumatoid factor, serum blocking factors, and the like.

Of particular interest to the present invention have been attempts to treat neoplastic diseases by the extracorporeal removal of circulating immune complexes from blood. Such complexes are formed by the binding of antigen to antibodies produced as a part of the humoral immune response to the antigen. It is thought that the formation of circulating immune complexes is part of the mechanism which turns off the immune response, in some cases prematurely. Removal of the immune complexes has usually been accomplished by binding the antibody component of the complex, typically using a protein-A immunoadsorbent material. Protein-A binds the $F_c$ region of certain subclasses of IgG, and the immunoadsorbent will thus non-specifically bind to the majority of circulating immune complexes in the blood, regardless of the nature of the antigen. While such treatments have lead to many examples of tumor regression, total remission of the tumor is rare.

For these reasons, it would be desirable to provide for improved methods and materials for treating neoplastic and other diseases by plasma perfusion. In particular, it would be desirable to provide materials and methods for removing particular antigens and circulating immune complexes from body fluids including such antigens in an antigen-specific manner.

2. Description of the Prior Art

U.S. Pat. No. 4,512,763 to Schneider discloses the use of an antibody immunoadsorbent for removing various components of a patient's blood, including immune complexes. Neither the feasibility nor the desirability of using antibodies specific for the antigen component of such complexes, however, is discussed. Plasma perfusion to remove circulating immune complexes by binding the $F_c$ region of the component antibody using protein-A is discussed in the following references: Kiprov et al. (1984) J. Biol. Res. Mod. 3:341-346; Jones et al. (1984) J. Biol. Res. Mod. 3:286-292; Besa et al. (1981) Am. J. Med. 71:1035-1040; European Patent Application 172 018 of Bensinger; European Patent Application 079 221 of Terman; and U.S. Pat. No. 4,614,513 to Bensinger.

SUMMARY OF THE INVENTION

Novel methods and materials are provided for extracorporeal removal of circulating immune complexes from a patient's blood for therapeutic purposes, particularly for the treatment of neoplastic, viral, and bacterial diseases. The methods rely on removing plasma from the patient and contacting the plasma with an immunoadsorbent material capable of binding an antigen associated with the disease, such as a tumor antigen, viral antigen, or bacterial antigen. Such contact results in the removal of both the free antigen and the circulating immune (antibody-antigen) complexes from the plasma. By varying the amount of plasma treated, the degree of antigen and circulating immune complexes removed from the patient's blood can be controlled, and the patient's immune response modulated in a desired manner.

The immunoadsorbent material may be any one of a wide variety of inert, non-toxic support materials having the desired antibody or other ligand bound thereto. Preferably, the immunoadsorbent comprises an antibody covalently attached to a silica substrate, where hydroxyl groups have been introduced to the silica and antibody attached to the hydroxyl by activation of cyanogen bromide and reacted with the antibody. Such a binding protocol has been found to maximize the activity and reactivity of the antibody while minimizing leakage of the antibody and other substances from the column during use. If such leakage occurs, it can present substantial problems when the column is used for in vivo plasma perfusion, as contemplated by the present invention.

While the present invention may be employed with a wide variety of previously known antigens, it may also be combined with an antigen identification procedure to identify previously unknown antigens or to tailor the method to remove antigens of particular interest to an individual patient. The identification procedure involves the non-specific removal of circulating immune complexes from the patient's blood. Typically, this is accomplished by extracorporeal plasma perfusion of the blood using a conventional non-specific receptor for such complexes, such as protein-A or anti-immunoglobulin antibody. The antigen and antibody can then be separated, allowing the antigen to be characterized or used to produce antibodies specific for that antigen. Alternatively, the antibodies from the complexes can themselves be used for the immunoadsorbent of the present invention, or anti-idiotypic antibodies can be prepared from the separated antibodies.

Surprisingly, the removal of circulating immune complexes and free antigen by immunoadsorption with an antibody specific for the free antigen has a number of advantages over the prior art. In particular, an improved therapeutic response is found. Such an improved therapeutic response might not have been expected in view of the removal of free antigen which is, of course, the basis for the initial immune response.

BRIEF DESCRIPTION OF THE DRAWINGS

FIG. 1 is an exploded view of the immunoadsorbent column of the present invention.

FIG. 2 is a diagrammatic representation of a system for extracorporeal plasma perfusion according to the principles of the present invention.

DESCRIPTION OF THE SPECIFIC EMBODIMENTS

According to the present invention, therapeutic plasma perfusion is performed with an immunoadsorbent material comprising an antibody bound to an inert, non-toxic support. The antibody is capable of binding to an antigen associated with a diseased state, and the immunoadsorbent material removes both free antigen and circulating immune complexes containing the antigen from the plasma. By returning the treated plasma to the patient, the level of antigen and circulating immune complexes in the blood can be controlled and the immune response modulated.

The present invention is useful for the treatment of a wide variety of neoplastic, viral, and bacterial diseases in humans and other mammals. Illustrative antigens related to neoplastic diseases include known tumor markers, such as $\alpha$-fetoprotein associated with hepatic cancer, carcinoembryonic antigen associated with various carcinomas, thioesterase associated with breast cancer, and cytokeratins associated with breast cancer, and the like. Of particular interest are tumor markers displaying terminal carbohydrate epitopes, designated Lewis$^a$ (Le$^a$), Lewis$^b$ (Le$^b$), and Lewis$^x$ (Le$^x$), particularly Le$^x$.

Illustrative viral and bacterial antigens will usually be viral coat and envelope proteins and bacterial membrane proteins capable of initiating a humoral immune response in an infected host.

In a preferred embodiment of the present invention, antigens of interest are isolated and identified from the plasma of a patient or group of patients prior to treatment. Such identification eliminates conjecture on which particular antigens are involved in the immune response. The antigen of interest may be isolated from the circulating immune complexes in the patient's blood by the technique taught in U.S. patent application Ser. No. 690,781, to Balint, Jr., filed on Jan. 11, 1985 now U.S. Pat. No. 4,681,870 and assigned to the assignee of the present invention. The disclosure of patent application Ser. No. 690,781, is incorporated herein by reference. Briefly, the circulating immune complexes are isolated from the patient's blood by extracorporeal plasma perfusion using a protein-A immunoadsorbent. The protein-A immunoadsorbent binds to the $F_c$ region of most subclasses of IgG, and the immunoadsorbent therefore removes the majority of circulating immune complexes regardless of the nature of the antigen (but does not remove antigen not bound to antibody). Although such non-specific removal results in a mixture of antigens in the removed immune complexes, it would be expected that the antigens will primarily be associated with the current diseased state. Thus, by eluting the complexes and separating the antigen from the antibody, large quantities of antigen can be obtained. After isolation, the antigen may be identified to allow selection of a particular immunoadsorbent specific for that antigen. Alternatively, in some cases it might be preferable to raise antibodies to the antigen in order to prepare a column intended for the individual patient or group of patients displaying a similar antigen. As a second alternative, it might be possible to utilize the isolated antibody directly for the preparation of the immunoaffinity column.

In many cases it will be possible to obtain suitable antibodies specific for tumor markers, viral proteins, and bacterial proteins from commercial sources. Such antibodies can be bound to a suitable solid phase support material, as described in detail hereinbelow, and the method of the present invention practiced with the resulting immunoadsorbent material.

In other cases, it will be necessary to prepare antibodies from the isolated antigens by conventional techniques. Briefly, antibodies may be obtained by injecting the desired antigen into a wide variety of vertebrates, such as mice, rats, rabbits, sheeps, and goats, in particular, rabbits. Usually, the animals are bled periodically with successive bleeds having improved titer and specificity. The antigens may be injected intramuscularly, intraperitoneally, subcutaneously, or the like. Usually, a vehicle is employed, such as complete or incomplete Freund's adjuvant. If desired, monoclonal antibodies can be prepared.

To obtain monoclonal antibodies, spleen cells from the immunized vertebrate, usually mouse, are immortalized. The manner of immortalization is not critical. Presently, the most common method is fusion with a myeloma fusion partner. Other techniques include EBV transformation, transformation with bare DNA, e.g., oncogenes, retroviruses, etc., or any other method which provides for stable maintenance of the cell line and production of monoclonal antibodies. A detailed technique for producing mouse x mouse monoclonal antibodies is taught by Oi and Herzenberg, in "Selected Methods in Cellular Immunology," Mishell and Shiigi (eds.), W. H. Freeman & Co., San Francisco (1980), pp. 351-372. Antibodies useful in the present invention may be of any immunoglobulin class, IgG, including IgG1, IgG2A, IgG2B, IgG3, and IgG4, IgA, IgD, IgE, and IgM, usually being either IgG or IgM.

Once the antibodies have been obtained, either commercially or by immunization with a desired antigen, the antibodies are bound to a solid phase support material. Suitable support materials may be organic, synthetic organic, or inorganic. Exemplary organic materials include cellulose, agarose, dextran, and cross linked products thereof. Suitable synthetic organic materials include polyacrylamide, polyamides, polyethylene, nylon and polyvinyl compounds, including polyvinyl chloride and polymethacrylates. Suitable inorganic materials include glass, and silica. Usually, the support material will be in the form of a bead, granule, or other particles suitable for packing in a conventional immunoaffinity column. Other solid phase supports, such as plates, may also find use.

Preferably, the solid phase support material will be a particulate silica, such as an amorphous silica including colloidal silica; a silica gel; a precipitated silica, a fumed silica, a microcrystalline silica, such as diatomite; or a crystalline silica, such as quartz. The silica should have a particle size in the range from about 45 to 120 mesh, usually being in the range from about 45 to 60 mesh.

In the preferred embodiment, the solid phase support will be formed from diatomite aggregates, usually the diatomite material will be calcined to remove any remaining organic material and to harden the surface of the aggregate in order to lessen breakage and degradation of the immunoadsorbent during use. The diatomite material consists primarily of silica (silicon dioxide) with lesser amounts of other minerals, including aluminum oxide, calcium oxide, magnesium oxide, ferric oxide, and the like. Usually, the diatomite material will comprise at least 80% silica, with less than 5% by weight of any other single mineral. Other impurities may be present in the diatomite, but care should be taken that such impurities are non-toxic and non-degradative to the biological fluid being treated. A particularly suitable solid phase silica (diatomite) support material may be obtained from the Johns-Mannville Corporation under the trade name Chromasorb ®.

Binding of the antibody to the solid phase support material will be covalent and may be accomplished by a variety of conventional techniques, depending primarily on the nature of the support material. Usually, the support material will be modified to introduce one or more binding moieties, such as hydroxyl, carboxyl, amino and/or imino functionalities. The moieties are then linked to the same or other functionally active sites on the antibody, typically amino groups.

Binding of the antibodies to the preferred diatomite support material may be accomplished by derivatizing the diatomite to introduce reactive hydroxyl and/or carboxyl groups, and reacting the derivatized diatomite with cyanogen bromide (CNBr). Hydroxyl groups (in addition to those hydroxyl groups occurring in the native structure of the diatomite) or amino groups may be introduced to the silica matrix by any suitable method. For example, the silica matrix may be acid washed, rinsed extensively with water, and dried. The acid washed silica is then reacted in a 5 to 10% solution of a silane, such as γ-aminopropyltriethoxysilane or γ-glycidoxypropyltrimethoxysilane. After a short incubation time, typically about 1 to 5 hours at 75° C., the silica matrix is again washed extensively with water and dried at an elevated temperature, typically about 100° C.

The cyanogen bromide coupling is then carried out as follows. Cyanogen bromide is dissolved in water, and the silica matrix is added to the water with the pH adjusted to about 11 to 11.5. The cyanogen bromide solution is added to the silica matrix, and the mixture is constantly stirred keeping the silica particles in suspension. The pH is maintained in the range from between about 11.0 and 11.5 by adding NaOH until pH stabilization occurs. The activated silica matrix is extensively washed with water, mixed with the solution of the desired antibody, the pH adjusted to the range from about 8.5 to 9.0, and the mixture held at 25° C. for several hours, typically from about 2 to 18 hours. After binding, the matrix is washed extensively with water, dried, and washed one time in an acid wash, pH 3.5, to remove non-covalently bound and acid labile antibody linkages. The silica matrix is then washed in water a final time and checked for pyrogens.

The method of the present invention relies on use of an immunoadsorbent prepared as described above to remove free antigen and circulating immune complexes containing the antigen from the blood of patients suffering from neoplastic, viral, and bacterial diseases. The removal of the antigen and immune complexes has a therapeutic effect which is believed to be derived from modulation and enhancement of the patient's own immune response to the antigens. Surprisingly, it is found that concurrent removal of both free antigen and circulating immune complexes results in an improved therapeutic response when compared with the non-specific removal of immune complexes, for example by adsorption with protein-A.

Removal of the antigens and immune complexes from the blood is accomplished by the plasma perfusion, where the cellular components of the blood including erythrocytes, polymorphonuclear leukocytes, lymphocytes, platelets, and the like, are initially separated. The plasma is then treated with the immunoadsorbent material, typically by passing through an immunoadsorbent column, and the treated plasma and cellular components returned to the patient. Usually, this treatment is accomplished using an extracorporeal shunt which allows treatment of substantially the entire blood volume, or any portion thereof. Alternatively, a small volume of the blood can be removed and treated. The cells will be returned to the patient immediately, and the treated plasma returned at a later time.

In performing the method of the present invention, it is not always desirable to remove all or substantially all of the free antigen and circulating immune complexes. At times, it may be desirable to remove only a portion of the antigens and immune complexes to achieve an optimum enhancement of the immune response.

While patients may be treated by the method of the present invention only a single time, usually multiple treatments will be performed over a period of weeks, months, or even years. Usually, at least four treatments will be made, more usually at least six treatments, frequently as many as ten or more treatments. Such treatments will usually be spaced apart by at least a week, usually by at least two weeks, and frequently by at least about a month, and sometimes more.

Referring now to FIG. 1, the construction of a suitable cartridge 10 for constructing an immunoaffinity column for use in the present invention will be described. The cartridge comprises a cylinder 12, a pair of retaining screens 14, and a pair of end caps 16. The end caps 16 each include a flange element 18 projecting from one surface thereof and a connector nipple 20 projecting from the other surface thereof. The connector nipple 20 includes an axial passage 22 therethrough to define inlet/outlet ports through the end caps 16. The cylinder 12 includes an annular groove 26 at each end thereof. The flange element 18 on each end cap 16 includes a mating ring 28 on the inner cylindrical surface thereof, which mating ring 28 engages the annular groove 26 when the end caps 16 are placed over the end of the cylinder 12. Each screen 14 includes a gasket 30 around its circumference, which gasket serves as a sealing member between the end caps 16 and the cylinder 12 when the cartridge 10 is assembled. To assemble cartridge 10, a first screen 14 is placed over one end of the cylinder 12, and an end cap 16 is fitted over the screen 14. The cylinder 12 is filled with the immunoadsorbent material as described above, and the assembly of the cartridge is completed by placing the remaining screen 14 and end cap 16 in place.

The dimensions of the cartridge 10 are not critical, and will depend on the desired volume of the immunoadsorbent material. The volume of the cylinder 12 typically will be in the range from about 50 to 500 cc, having a diameter in the range from about 4 to 8 cm, and a length in the range from about 5 to 10 cm.

Immunoaffinity columns prepared from the cartridges 10 and containing a suitable amount of the immunoadsorbent material may be sterilized, typically with a gas sterilant such as ethylene oxide, and either used immediately or sealed and stored for later use. Prior to use, the column should be washed with normal saline, followed by a wash with normal saline containing heparin or other suitable anti-coagulant, such as, anti-coagulant citrate dextrose (ACD).

The method of the present invention may be performed continuously or discontinuously, depending on the desired therapy, availability of equipment, and the like. Discontinuous treatment is performed by removing a discrete volume of blood from the patient, typically from 100 to 600 ml, usually from about 400 to 500 ml, by conventional venous phlebotomy. The withdrawn blood is immediately separated into its cellular components and plasma, typically by centrifugation at about 800 to 1600 rpm for from about 5 to 20 min. Alternatively, a semipermeable membrane may be used. After separation, the cellular components are immediately reinfused into the patient by normal procedures, such as venous infusion. The plasma is then applied to the column 10 at a flow rate in the range from about 10 to 30 ml/min. Normal precautions should be taken to assure that the plasma flows evenly through the column and that all the plasma is exposed to the protein. The immunoadsorption will thus require from about 5 to 60 min., usually about 15 to 45 min., depending on the flow rate and volume of plasma. After the entire volume has been treated, it is returned to the patient by venous infusion or other circulatory access.

A system for continuously performing extracorporeal plasma perfusion according to the method of the present invention is illustrated in FIG. 2. An immunoaffinity column 11 (packed with the immunoadsorbent described above) is connected to a cell separator 40 to receive separated plasma therefrom. The cell separator 40 may be a continuous flow separator, such as a Century 2997, available from Cobe Laboratories, Golden, Colo., or may comprise a semi-permeable membrane which allows passage of the plasma and blood proteins, but inhibits passage of the cellular elements of the blood. In the case of a semi-permeable membrane, a blood pump will be required to pass the blood through the plasma separator. A second pump is used to draw the blood plasma across the membrane and effect separation. Suitable blood pumps include tube and peristaltic pumps where the blood is isolated from the pumping machinery to prevent contamination. The blood will pass through the cell separator 40 at a rate in the range from about 10 to 50 ml/min., typically until a total volume of about two liters of plasma have been passed through the immunoadsorbent. The blood cells are then mixed with the treated plasma and the recombined blood returned to the patient. Typically, a microfilter 44 is provided at the outlet of the treatment column 11 to prevent passage of macroscopic particles or air bubbles which might be lost from column 11.

Although the foregoing invention has been described in some detail by way of illustration and example for purposes of clarity of understanding, it will be obvious that certain changes and modifications may be practiced within the scope of the appended claims.

What is claimed is:

1. A method for treating antigen-related disease in a patient, said method comprising the steps of:
   (a) withdrawing plasma from the patient,
   (b) contacting the patient's plasma with an immunoadsorbent which nonspecifically binds circulating immune complexes regardless of the immune complexes' antigen component;
   (c) separating from the plasma the bound immune complexes;
   (d) identifying the predominant antigen from the immune complexes which antigen associated with the disease;
   (e) treating additional patient plasma with a second immunoadsorbent specific for said identified predominant antigen; and
   (f) returning at least the treated plasma to the patient.

2. The method of claim 1 wherein said second immunoadsorbent specific for the identified antigen is an antibody.

3. The method of claim 2, wherein said antibody is isolated from the bound immune complexes.

4. The method of claim 2, wherein said antibody is antisera obtained from an animal which has been immunized with the identified antigen.

5. The method of claim 4, wherein said antibody is a monoclonal antibody.

6. The method of claim 1, wherein the nonspecific immunoadsorbent is protein A.

7. The method of claim 1, wherein the nonspecific immunoadsorbent is an anti-immunoglobulin.

8. The method of claim 7, wherein said anti-immunoglobulin antibody is an anti-IgG antibody.

9. The method of claim 1, wherein antigen is removed from the separated immune complexes prior to the step of identifying the antigen.

10. The method of claim 1, wherein the patient's plasma is withdrawn a second time before the step of treating.

* * * * *